United States Patent [19]

Brown-Milants et al.

[11] Patent Number: 5,537,702
[45] Date of Patent: Jul. 23, 1996

[54] TOMOGRAPHIC PILLOW WITH UPPER ARM SUPPORT

[75] Inventors: Audree J. Brown-Milants, New York; Titus George, Elmont, both of N.Y.

[73] Assignee: Mount Sinai School of Medicine of the City University of New York, New York, N.Y.

[21] Appl. No.: 492,853

[22] Filed: Jun. 20, 1995

[51] Int. Cl.⁶ .......................... A61G 15/00; A47C 20/02; A47G 9/00
[52] U.S. Cl. .................................. 5/632; 5/637; 128/845; 128/878
[58] Field of Search .............................. 5/632, 636, 637, 5/646, 647; 128/845, 869, 870, 878

[56] References Cited

U.S. PATENT DOCUMENTS

| | | | |
|---|---|---|---|
| 4,097,038 | 6/1978 | Jansen | 5/638 |
| 4,625,232 | 5/1981 | Stonich | 5/647 |
| 5,007,122 | 4/1991 | Daughdrill | 5/637 |
| 5,214,814 | 6/1993 | Fremita et al. | 5/646 |
| 5,337,760 | 8/1994 | Nichols | 5/637 |
| 5,467,782 | 11/1995 | Wiseman | 5/646 |

Primary Examiner—Alexander Grosz
Attorney, Agent, or Firm—Brumbaugh, Graves, Donohue & Raymond

[57] ABSTRACT

In accordance with the invention, there is disclosed a pillow for holding and restraining a patient's head and arms during tomographic imaging, said pillow comprising a bottom panel, two side panels, and a back panel, each of said side panels having a front-facing surface which is rearwardly and upwardly inclined from the bottom thereby providing, when a patient's head is placed within the pillow, a surface against which each of the patient's upper arms may rest, each said inclined surface further having an adjustable strap for restraining the upper arm against the inclined surface, said pillow further comprising a pair of adjustable straps on the back panel for engaging and restraining the patient's wrist or for grasping by the patient. The pillow also optionally comprises extra straps on the side for restraining or grasping, and straps on the bottom for attaching the pillow to a imaging table or the like.

6 Claims, 2 Drawing Sheets

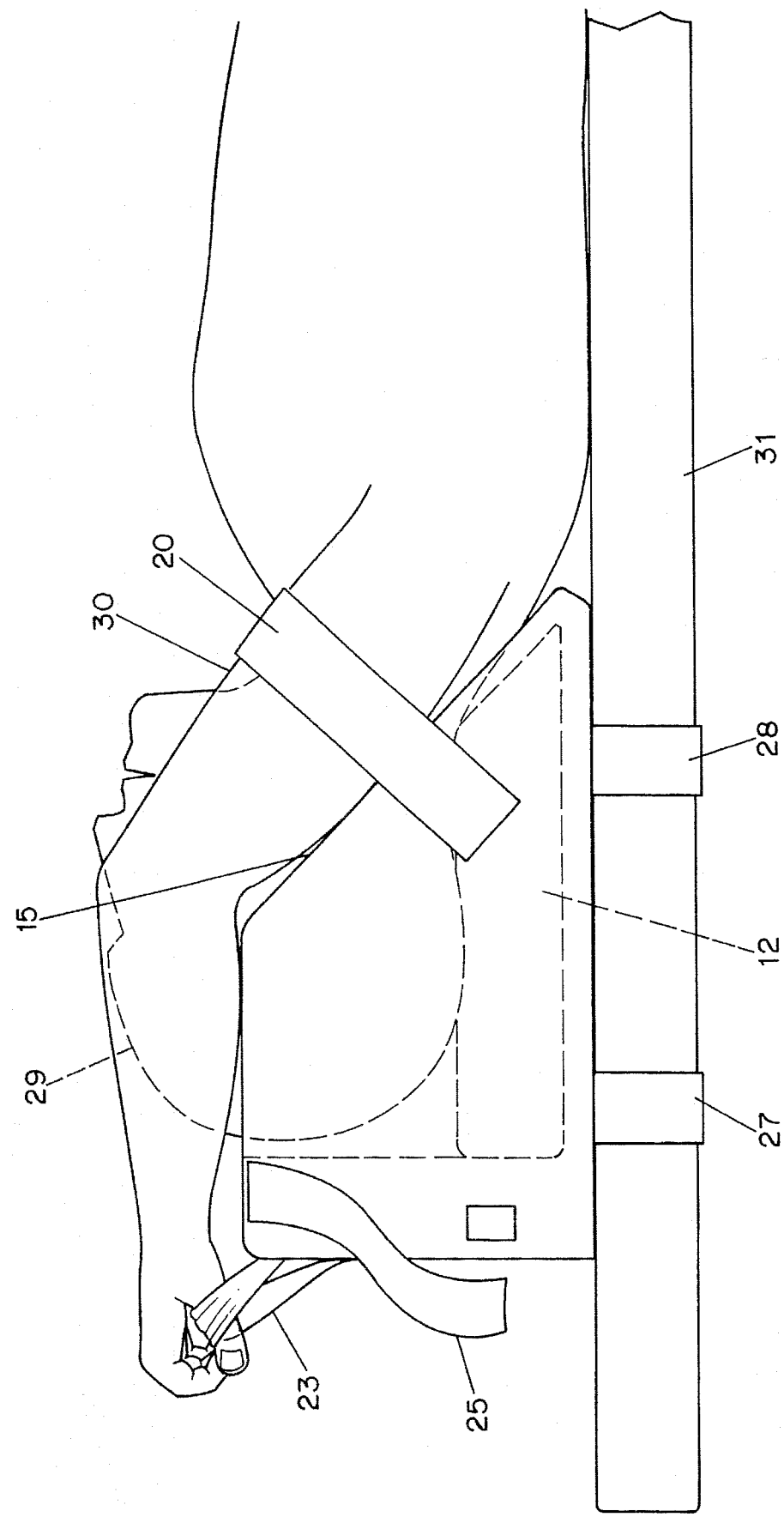

TOMOGRAPHIC PILLOW WITH UPPER ARM SUPPORT

BACKGROUND OF THE INVENTION

The present invention relates to a pillow device for use during tomographic imaging of the body.

Tomographic imaging involves the taking of very precise multiple images of the body. During imaging, the patient must lie immobile, often in a position that is uncomfortable or, in the case of elderly patients, even painful. This is particularly true where the imaging is of the upper body, since the arm or arms must be raised above the head so as not to interfere with the imaging.

BRIEF SUMMARY OF THE INVENTION

In accordance with the invention, a tomographic pillow device is provided. The pillow is configured so as to retain the patient's arms immobile away from the area to be imaged. The pillow is intended to reduce or eliminate the discomfort previously associated with tomographic imaging. Indeed, with the present invention it has been found that patients are actually able to relax during the imaging procedure, which contributes to the ability of the patient to remain immobile.

BRIEF DESCRIPTION OF THE DRAWINGS

The invention will now be described in further detail with reference to the accompanying drawings where

FIG. 2 is a side cutaway view of the pillow in use during imaging.

DESCRIPTION OF THE PREFERRED EMBODIMENT

Figure 1:
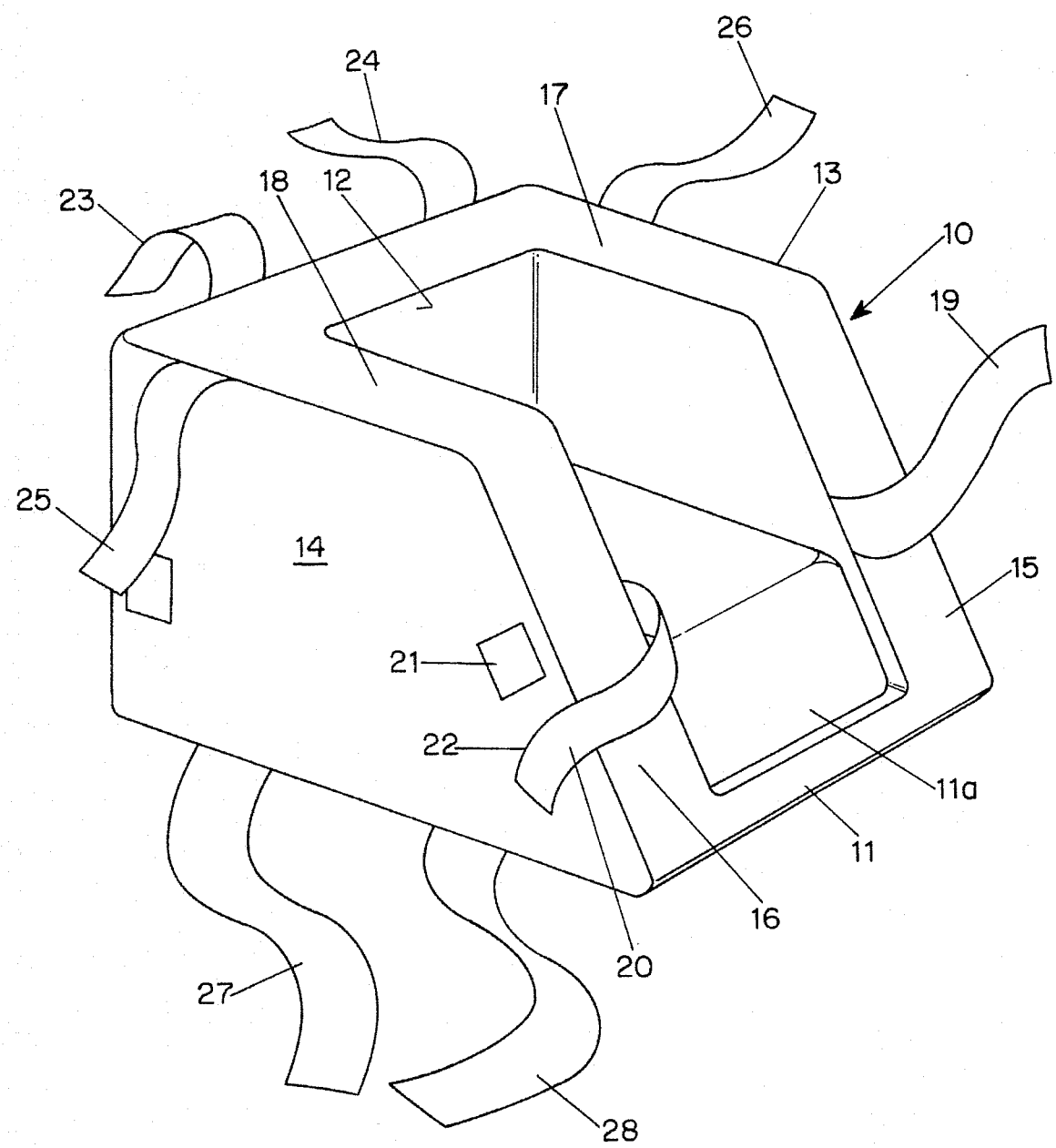
FIG. 1 is a perspective view of the tomographic pillow.

The tomographic pillow according to the invention is preferably of foam rubber construction, typically covered with plastic or fabric. Plastic is preferred for ease of cleaning, particularly in a hospital environment.

Looking of FIG. 1, the pillow 10 is comprised of a bottom panel 11, a back panel 12 and side panels 13, 14. These panels form an open-front and open-top box in which the patient may rest his or her head. There is also provided a removable cushion 11a. Depending upon the size of the patient, or desired angle of the neck and head during imaging, the cushion may or may not be used.

The sides 13, 14 of the pillow each have front facing inclined surfaces 15, 16, and flat horizontal top surfaces 17, 18.

Attached to each of the front facing inclined surfaces is a strap 19, 20, permanently affixed to the pillow at one end and adjustable and detachable, e.g. by Velcro® surfaces 21, 22, at the other. As will be described with reference to FIG. 2, these straps hold the patient's upper arms against the inclined surfaces and away from the upper body during imaging.

There are also two additional pairs of straps similarly attached (i.e., one end fixedly, the other end detachably) to the rear portion of the pillow. One pair of straps 23, 24, is on the rear panel 12 of the pillow. These straps may be adjusted at their respective removable ends, and may either restrain the patient's wrists, or provide loops which the patient may grasp by the hands. The latter is often preferable since it gives the patient a feeling of freedom while maintaining immobility.

The other pair of straps 25, 26 extend from the rear of the side panels. These straps provide an alternate means for restraining the patient's wrists or providing loops for grasping.

Finally, there is at least one strap 27, and preferably two 27, 28, on the bottom of the pillow, permanently attached at one side of the bottom and removably and adjustably attached at the other side. These straps permit the pillow to be firmly attached to an imaging table or the like. Two such straps are preferred so as to limit any twisting motion of the pillow.

Referring to FIG. 2, the patient's head 29 rests on the cushion 12. Each arm is raised such that the upper arm 30 rests against the inclined surface 15, where it is restrained by strap 20. As shown, the patient grips strap 23. Alternatively, strap 23 may be placed over the patient's wrist and tightened in place. Similarly, strap 25 or 26 can be used for gripping or restraining.

In use, the pillow may be placed upon an imaging table 31. Straps 27 extend from one side of the pillow, under the table, and to the other side of the pillow. By using Velcro® attachments or the like, these straps may be pulled tight, thereby firmly holding the pillow on the table.

We claim:

1. A pillow for holding and restraining a patient's arms during tomographic imaging, said pillow comprising a a generally horizontal bottom panel, two generally vertical side panels, and a generally vertical back panel, each of said side panels having a front-facing surface which is rearwardly and upwardly inclined from the bottom thereby providing, when a patient's head is placed within the pillow, a surface against which each of the patient's upper arms may rest, each said inclined surface further having an adjustable strap for restraining an upper arm against the inclined surface, said pillow further comprising a pair of adjustable straps on the back panel for engaging and restraining the patient's wrist or for grasping by the patient.

2. A pillow according to claim 1, said pillow being of foam construction covered with plastic.

3. A pillow according to claim 2, further comprising at least one adjustable strap on the bottom of the pillow for holding the pillow on an imaging table.

4. A pillow according to claim 2, further comprising an additional pair of straps, one said strap on a rear portion of each side panel, said straps providing an alternative restraining or gripping means for the patient's wrists or hands respectively.

5. A pillow according to claim 3, further comprising an additional pair of straps, one said strap on a rear portion of each side panel, said straps providing an alternative restraining or gripping means for the patient's wrists or hands respectively.

6. A pillow according to claim 2, further comprising a removable cushion on said bottom panel and between the side panels for supporting the patient's head.

* * * * *